US012728131B2

(12) United States Patent
Almirante et al.

(10) Patent No.: US 12,728,131 B2
(45) **Date of Patent: *Sep. 8, 2026**

(54) COMPOSITIONS FOR THE TREATMENT OF GLAUCOMA AND OCULAR HYPERTENSION

(71) Applicant: Nicox S.A., Valbonne (FR)

(72) Inventors: Nicoletta Almirante, Milan (IT); Stefania Brambilla, Merone (IT); Francesco Impagnatiello, Milan (IT); Elena Bastia, Milan (IT); Corinna Galli, Marcallo con Casone (IT)

(73) Assignee: NICOX S.A., Valbonne (FR)

( * ) Notice: Subject to any disclaimer, the term of this patent is extended or adjusted under 35 U.S.C. 154(b) by 989 days.

This patent is subject to a terminal disclaimer.

(21) Appl. No.: 17/760,012

(22) PCT Filed: Feb. 3, 2021

(86) PCT No.: PCT/EP2021/052480

§ 371 (c)(1),
(2) Date: Aug. 3, 2022

(87) PCT Pub. No.: WO2021/156275

PCT Pub. Date: Aug. 12, 2021

(65) Prior Publication Data

US 2023/0069076 A1 Mar. 2, 2023

(30) Foreign Application Priority Data

Feb. 5, 2020 (EP) .................................... 20155635
Feb. 5, 2020 (EP) .................................... 20155638
Feb. 5, 2020 (EP) .................................... 20155640

(51) Int. Cl.
*A61K 9/00* (2006.01)
*A61K 31/519* (2006.01)
*A61K 31/5575* (2006.01)
*A61K 31/5578* (2006.01)

(52) U.S. Cl.
CPC .......... *A61K 31/519* (2013.01); *A61K 9/0048* (2013.01); *A61K 31/5575* (2013.01); *A61K 31/5578* (2013.01)

(58) Field of Classification Search
None
See application file for complete search history.

(56) References Cited

U.S. PATENT DOCUMENTS 11,980,618 B2 * 5/2024 Almirante .............. A61K 47/44
2002/0168424 A1 11/2002 Mohsen
2016/0158182 A1 * 6/2016 Ongini .................. A61K 45/06
514/249
2021/0322413 A1 10/2021 Almirante et al.

FOREIGN PATENT DOCUMENTS

CN 101102774 A 1/2008
CN 106999452 A 8/2017
CN 112566670 A 3/2021
WO 2006/074872 A1 7/2006
WO 2014/170264 A1 10/2014
WO 2015/007552 A1 1/2015
WO 2016/079142 A1 5/2016
WO 2020/030489 A1 2/2020

OTHER PUBLICATIONS

Office Action received for Chinese Patent Application No. 202180012464.2, mailed on Jan. 4, 2024, 9 pages (3 pages of English Translation and 6 pages of Original Document).
Impagnatiello et al: "NCX 1741, a novel NO-donating derivative of the Commercial Relationships Disclosure: Intraocular pressure (IOP) studies", Apr. 8, 2019, Retrieved from the Internet: www.nicox.com/assets/files/Impagnatiello ARVO-2019_03272019.pdf [retrieved-on May 11, 2021].
Flores Toque et al: "Synthesis and Pharmacological Evaluations of Sildenafil Analogues for Treatment of Erectile Dysfunction", Journal of Medicinal Chemistry, vol. 51, No. 9, May 1, 2008, pp. 2807-2815.
International Search Report and Written Opinion mailed May 20, 2021 issued in PCT Application No. PCT/EP2021/052480.

* cited by examiner

*Primary Examiner* — Katherine Peebles
(74) *Attorney, Agent, or Firm* — ArentFox Schiff LLP

(57) ABSTRACT

The invention relates to ophthalmic compositions comprising a nitric oxide releasing phosphodiesterase type 5 inhibitor (NO-PDE5 inhibitor) and a prostaglandin analog, and to the use of these ophthalmic compositions for the treatment of all forms of glaucoma or ocular hypertension as well as eyes diseases or conditions associated with elevated intraocular pressure. The NO-PDE5 inhibitor is selected from the following compounds: [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy) hexanoate (Compound (1)), [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 3-[(2S)-2,3-bis(nitrooxy)propoxy]propanoate (Compound (1A)) or 2-{4-[3-(5-Ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy) propoxy]propanoate (Compound (2)). The prostaglandin analog is selected from latanoprost, bimatoprost, travoprost or tafluprost.

12 Claims, No Drawings

COMPOSITIONS FOR THE TREATMENT OF GLAUCOMA AND OCULAR HYPERTENSION

CROSS-REFERENCE TO RELATED APPLICATIONS

This application is a 35 U.S.C. 371 National Phase of PCT Application No. PCT/EP2021/052480, filed on Feb. 3, 2021, which claims priority to EP application Ser. Nos. 20/155,635.4, filed Feb. 5, 2020, 20155638.8, filed Feb. 5, 2020 and 20155640.4, filed Feb. 5, 2020. The contents of each application are hereby incorporated by reference in their entirety.

The invention relates to ophthalmic compositions comprising a combination of a nitric oxide releasing phosphodiesterase type 5 inhibitor (NO-PDE5 inhibitor) and a prostaglandin analog and to a method of treatment of all forms of glaucoma or ocular hypertension as well as eye diseases or conditions associated with elevated intraocular pressure using such compositions. The NO-PDE5 inhibitor is selected from the following compounds:

[(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy) hexanoate (Compound (1));

[(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy)propoxy]propanoate (Compound (1A));

2-{4-[3-(5-Ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate (Compound (2)), and the prostaglandin analog is selected from latanoprost, bimatoprost, travoprost or tafluprost.

[(2S)-1-(4-{[(3-Chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate (Compound (1)) has the following formula (1)

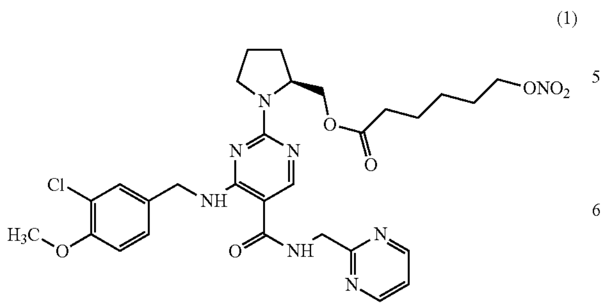

[(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 3-[(2S)-2,3-bis(nitrooxy)propoxy]propanoate (Compound (1A)) has the following formula (1A)

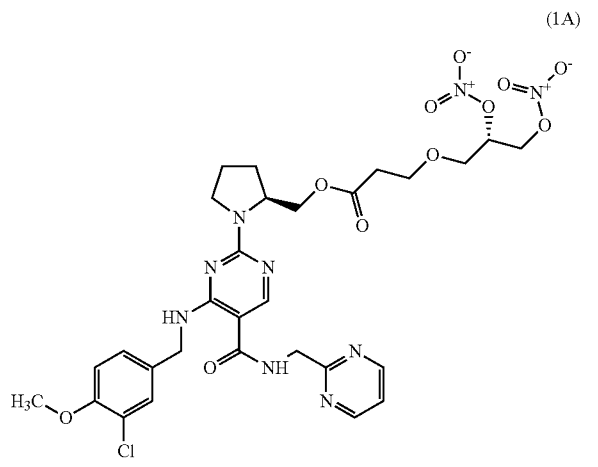 [SMILES: COc1ccc(CNc2nc(N3CCC[C@H]3COC(=O)CCOC[C@@H](CO[N+](=O)[O-])O[N+](=O)[O-])ncc2C(=O)NCc2ncccn2)cc1Cl]

2-{4-[3-(5-Ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate (Compound (2)) has the following formula (2)

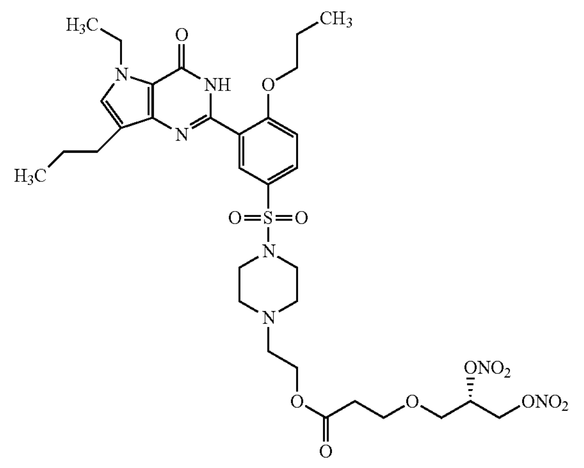

Glaucoma is a disease characterized by progressive optic nerve damage and, ultimately, total loss of vision. Since there is a good correlation between intraocular pressure control and prevention/reduction of glaucomatous damage in Primary Open-Angle Glaucoma (POAG) patients, several therapeutic agents have been developed to reduce intraocular pressure (Weinreb Robert N. et al. JAMA. 2014 May 14; 311(18): 1901-1911).

It is known that elevated intraocular pressure can be at least partially controlled by administering drugs that increase the drainage of aqueous humor from the eye, such as the prostaglandin analogs (i.e. latanoprost or bimatoprost, travoprost or tafluprost) or drugs that reduce the production of aqueous humor including beta-blockers (i.e. timolol, betaxolol, levobunolol) and carbonic anhydrase inhibitors (i.e. acetazolamide, dorzolamide or brinzolamide).

Currently, prostaglandin analogs are the first-line treatment for most glaucoma patients. These drugs are highly effective and only require once-a-day dosing, making them an ideal choice for a single-drug treatment regimen. However, in many cases, prostaglandin analogs are not sufficient to achieve sufficient IOP reduction compared to starting baseline values.

Moreover, several clinical trials showed that each mmHg of decreased IOP is related to an approximately 10% to 20% lowering of risk of vision loss progression (Heijl et al. Arch Ophthalmol. (2002) 120: 1268-1279; Heijl The Lancet (2015) 385: 1264-1266).

Recently, fixed-dose combinations of the various prostaglandin analogs with timolol have been introduced in the market; these include Xalacom, a fixed-dose combinations of latanoprost and timolol; DuoTrav, a combination of travoprost and timolol; Ganfort, which combines bimatoprost with timolol.

These fixed-dose combinations provide better intraocular pressure control because of the complementary modes of action; indeed, prostaglandin analogs are outflow-enhancing drugs while timolol reduces the production of aqueous humor within the eye.

However, fixed combinations containing timolol as one of the active ingredient brings intrinsic limitations associated to the use of this specific class of agents; for example, timolol, which is a beta-blocker, is contraindicated in patients suffering of asthma, severe chronic obstructive pulmonary disease, sinus bradycardia, impotence, depression, confusion and memory loss.

Most recently, an alternative fixed combination containing latanoprost and the Rho kinase inhibitor netarsudil was approved by the FDA (Rocklatan). EP 1 459 743 discloses Rho kinase inhibitors as therapeutic agents for the reduction of IOP in patients with open-angle glaucoma or ocular hypertension based on a new mechanism of action. Specifically, Rho kinase inhibitors seem to increase aqueous humor outflow from the trabecular meshwork outflow pathway. Clin. Invest. (2014) 4(5), 391-393. In spite of their IOP-lowering profile, Rho kinase inhibitors raised, however, several safety concerns including conjunctival hyperemia. Therefore, the tolerability of the latanoprost-netarsudil combination is critical to its commercial success.

It is known that adverse effects of topical hypotensive therapy for glaucoma, such as conjunctival hyperemia, ocular discomfort and itching, are leading causes of non-adherence for glaucoma patients.

US 2014/0018350 discloses the combined use of tafluprost with isopropyl(6-{[4-(pyrazol-1-yl)benzyl](pyridin-3-ylsulfonyl)aminomethyl}pyridin-2-ylamino)acetate that is a selective EP2 receptor agonist. The experimental results show that at 6 hours after the combined administration of the two compounds lowers intraocular pressure to greater extent compared to each compound administered alone. However, US 2014/0018350 does not describe the tolerability of this combination.

U.S. Pat. No. 7,816,399 discloses that the administration of latanoprost in combination with nipradilol has greater intraocular pressure-lowering effect than the administration of the single drugs.

Nipradilol is an alpha-beta blocker and it has nitric oxide donating action, therefore adding nipradilol to latanoprost may result in additional IOP lowering effects via multiple mechanisms, namely: reduced aqueous humor formation via β-blocking activity and increased aqueous humor drainage via blockade of α-adrenoreceptors and/or increased nitric oxide signaling.

WO 2015/007552 discloses compositions comprising a 4-nitrooxybutan-1-ol alkyl ester as a nitric oxide donor and a prostaglandin analog useful in controlling elevated intraocular pressure associated with glaucoma or ocular hypertension consequent to other diseases or conditions. WO 2015/007552 does not provide experimental results related to the intraocular pressure lowering activity of the disclosed combinations.

EP 3 220 905 discloses a compositions comprising a nitric oxide-releasing isomannide derivative and a prostaglandin F2a analog; data obtained in ocular normotensive and hypertensive rabbits show that these combinations have an enhanced and sustained intraocular pressure lowering effect compared to the compounds administered alone.

Vyzulta (latanoprostene bunod) is a nitric oxide-donating latanoprost in which the NO-donating molecule (butanediol mononitrate) is covalently linked to the prostaglandin scaffold through an ester bond. Vyzulta works as it is metabolized into two moieties, latanoprost acid and butanediol mononitrate further processed to release nitric oxide.

Published results show that latanoprostene bunod (0.024%) produced greater mean IOP reduction (reduction in mean diurnal IOP of 9.0 mmHg) compared to latanoprost (0.005%) (reduction in mean diurnal IOP of 7.77 mmHg) in the phase 2 dose-ranging VOYAGER study. Weinreb R N, et al. Br J Ophthalmol 2015; 99:6:738-45.

Several studies showed that at cellular level, nitric oxide binds to the soluble guanylate cyclase enzyme (sGC) and increases the production of cyclic guanosine monophosphate (cGMP) in the trabecular meshwork and in the Schlemm's canal tissues. CyclicGMP then activates a series of mechanisms to facilitate conventional aqueous humor drainage and reduce intraocular pressure (Cavet et al., Invest Ophthalmol Vis Sci. 2014, 5005-5015).

PCT/EP/2019/070597 discloses a new class of nitric oxide releasing phosphodiesterase type 5 inhibitors (NO-PDE5-inhibitors) having intraocular pressure-lowering activity and good tolerability profile. PCT/EP/2019/070597 does not provide results related to the intraocular pressure lowering activity of combinations comprising the NO-PDE5 inhibitors and other IOP lowering drugs.

WO 2017/085056 and WO 2018/215433 disclose dual-pharmacology nitric oxide-donating PDE5 inhibitors that are useful in the treatment of a variety of diseases where a disturbed cGMP balance occurs and/or PDE inhibition is thought to be beneficial, in particular for the treatment of diabetic patients; glaucoma is cited therein among others as a preferred disease.

WO 2017/085056 discloses the results of in vitro studies showing that these nitric oxide-releasing PDE5 inhibitors are able to activate soluble guanylate cyclase and have greater PDE5 inhibitory activity than the known PDE5 inhibitor, sildenafil. However, both the references do not provide any experimental data related to the intraocular pressure lowering activity of these nitric oxide-releasing PDE5 inhibitors.

Despite the availability of effective drugs, new treatments of elevated intraocular pressure and glaucoma remain of interest for a more effective management of these diseases and pathological conditions.

The present invention relates to alternative ophthalmic compositions able to decrease elevated intraocular pressure in patients with glaucoma or elevated intraocular pressure, as well as to methods of lowering intraocular pressure utilizing these compositions.

The ophthalmic compositions of the present invention, which comprise a NO-PDE5 inhibitor selected from: [(2S)-

1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate, [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy)propoxy]propanoate, 2-{4-[3-(5-Ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate together with a prostaglandin analog selected from latanoprost, bimatoprost, travoprost or tafluprost, are able to effectively decrease elevated intraocular pressure. The complementary modes of action of the two active ingredients should result in a robust and sustained IOP reduction that, combined with a good tolerability, would allow these compositions to become viable options for the treatment of glaucoma and ocular hypertension. The good tolerability could also envisage an improvement of patient adherence to this treatment strategy.

Therefore, the invention provides an alternative intraocular pressure lowering ophthalmic compositions useful to prevent or treating glaucoma, ocular hypertension or eyes diseases and conditions associated with increased ocular pressure.

The invention provides an ophthalmic compositions comprising i) a nitric oxide releasing phosphodiesterase type 5 inhibitor selected from:

[(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate (Compound (1)) or a pharmaceutically acceptable salt thereof, [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy) propoxy] propanoate (Compound (1A)) or a pharmaceutically acceptable salt thereof, or 2-{4-[3-(5-Ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate (Compound (2)) or a pharmaceutically acceptable salt thereof, and ii) a prostaglandin analog selected from latanoprost, bimatoprost, travoprost or tafluprost.

The nitric oxide releasing phosphodiesterase type 5 inhibitor salts used in the present invention include salts of the NO-PDE5 inhibitor free base with ocular tolerable acids including citric acid, oxalic, malic, tartaric, succinic acid, acetic acid, propionic acid, lactic acid, hydrochloric acid hydrobromic acid, sulfuric acid, phosphoric acid, nitric acid, methanesulfonic acid, ethanesulfonic acid or benzenesulfonic acid.

Some examples of pharmaceutical acceptable salts of [(2S)-1-(4-{[(3-chloro-4-methoxyphenyl) methyl]amino}-5-{[(pyrimidin-2-yl)methyl]carbamoyl}pyrimidin-2-yl)pyrrolidin-2-yl]methyl 6-(nitrooxy)hexanoate (Compound (1)) are the following compounds:

2-hydroxypropane-1,2,3-tricarboxylic acid [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate (1/1);

(2E)-but-2-enedioic acid [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate (1/1);

(2Z)-but-2-enedioic acid [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate (1/1);

An example of a pharmaceutical acceptable salt of [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy) propoxy]propanoate (Compound (1A)) is:

2-hydroxypropane-1,2,3-tricarboxylic acid [(2S)-1-(4-{[(3-chloro-4-methoxy phenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy)propoxy]propanoate (1/1).

Some examples of preferred pharmaceutical acceptable salts of 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis (nitrooxy)propoxy] propanoate (Compound (2)) are the following compounds:

2-hydroxypropane-1,2,3-tricarboxylic acid 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate (1/1);

2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate hydrogen chloride (1/2).

The preferred prostaglandin analog for use in the present invention is latanoprost.

Another preferred embodiment of the invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 6-(nitrooxy)hexanoate or a pharmaceutical acceptable salt thereof and latanoprost.

Another embodiment of the invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate or a pharmaceutical acceptable salt thereof and bimatoprost.

Another embodiment of the invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate or a pharmaceutical acceptable salt thereof and travoprost.

Another embodiment of the invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate or a pharmaceutical acceptable salt thereof and tafluprost.

Another preferred embodiment of the invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 3-[(2S)-2,3-bis(nitrooxy) propoxy]propanoate or a pharmaceutical acceptable salt thereof and latanoprost.

Another preferred embodiment of the invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 3-[(2S)-2,3-bis(nitrooxy) propoxy]propanoate or a s pharmaceutical acceptable alt thereof and bimatoprost.

Another embodiment of the invention provides ophthalmic compositions comprising [(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 3-[(2S)-2,3-bis(nitrooxy) propoxy]propanoate or pharmaceutical acceptable a salt thereof and travoprost.

Another embodiment of the invention provides ophthalmic compositions comprising [(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 3-[(2S)-2,3-bis(nitrooxy) propoxy]propanoate or a pharmaceutical acceptable salt thereof and tafluprost.

Another preferred embodiment of the invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate or a pharmaceutical acceptable salt thereof and latanoprost.

Another preferred embodiment of the invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate or a pharmaceutical acceptable salt thereof and bimatoprost.

Another embodiment of the invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate or a pharmaceutical acceptable salt thereof and travoprost.

Another embodiment of the invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate or a pharmaceutical acceptable salt thereof and tafluprost.

Another embodiment of the invention provides ophthalmic compositions comprising 2-hydroxypropane-1,2,3-tricarboxylic acid [(2S)-1-(4-{[(3-chloro-4-methoxyphenyl) methyl]amino}-5-{[(pyrimidin-2-yl)methyl] carbamoyl}pyrimidin-2-yl) pyrrolidin-2-yl]methyl 6-(nitrooxy)hexanoate (1/1) and a prostaglandin analog selected from latanoprost, bimatoprost, travoprost or tafluprost.

Another embodiment of the invention provides ophthalmic compositions comprising 2-hydroxypropane-1,2,3-tricarboxylic acid [(2S)-1-(4-{[(3-chloro-4-methoxyphenyl) methyl]amino}-5-{[(pyrimidin-2-yl)methyl] carbamoyl}pyrimidin-2-yl)pyrrolidin-2-yl]methyl 3-[(2S)-2,3-bis(nitrooxy)propoxy]propanoate (1/1) and a prostaglandin analog which is selected from latanoprost, bimatoprost, travoprost or tafluprost.

Another preferred embodiment of the invention provides ophthalmic compositions comprising 2-hydroxypropane-1, 2,3-tricarboxylic acid 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis (nitrooxy)propoxy]propanoate (1/1) and a prostaglandin analog selected from latanoprost, bimatoprost, travoprost or tafluprost.

Another embodiment of the invention provides ophthalmic compositions comprising (2E)-but-2-enedioic acid [(2S)-1-(4-{[(3-chloro-4-methoxyphenyl) methyl]amino}-5-{[(pyrimidin-2-yl)methyl]carbamoyl}pyrimidin-2-yl)pyrrolidin-2-yl]methyl 6-(nitrooxy)hexanoate (1/1) and a prostaglandin analog selected from latanoprost, bimatoprost, travoprost or tafluprost.

Another embodiment of the invention provides ophthalmic compositions comprising (2Z)-but-2-enedioic acid [(2S)-1-(4-{[(3-chloro-4-methoxyphenyl) methyl]amino}-5-{[(pyrimidin-2-yl)methyl]carbamoyl}pyrimidin-2-yl)pyrrolidin-2-yl]methyl 6-(nitrooxy) hexanoate (1/1) and a prostaglandin analog selected from latanoprost, bimatoprost, travoprost or tafluprost.

Another embodiment of the invention provides ophthalmic compositions comprising 2-hydroxypropane-1,2,3-tricarboxylic acid 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate (1/1) and a prostaglandin analog selected from latanoprost, bimatoprost, travoprost or tafluprost.

Another embodiment of the invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate hydrogen chloride (1/2) and a prostaglandin analog selected from latanoprost, bimatoprost, travoprost or tafluprost.

The prostaglandin analogs mentioned above are commercially available: latanoprost (chemical name, propan-2-yl (Z)-7-[(1R,2R,3R,5S)-3,5-dihydroxy-2-[(3R)-3-hydroxy-5-phenylpentyl] cyclopentyl]hept-5-enoate); bimatoprost (chemical name, (Z)-7-[(1R,2R,3R,5S)-3,5-dihydroxy-2-[(E,3S)-3-hydroxy-5-phenylpent-1-enyl]cyclopentyl]-N-ethylhept-5-enamide); travaprost (chemical name, propan-2-yl (Z)-7-[(1R,2R,3R,5S)-3,5-dihydroxy-2-[(E,3R)-3-hydroxy-4-[3-(trifluoromethyl)phenoxy]but-1-enyl] cyclopentyl]hept-5-enoate); tafluprost (chemical name is propan-2-yl (Z)-7-[(1R,2R,3R,5S)-2-[(E)-3,3-difluoro-4-phenoxybut-1-enyl]-3,5-dihydroxycyclopentyl]hept-5-enoate).

The [(2S)-1-(4-{[(3-chloro-4-methoxyphenyl)methyl] amino}-5-{[(pyrimidin-2-yl)methyl]carbamoyl}pyrimidin-2-yl)pyrrolidin-2-yl]methyl 6-(nitrooxy)hexanoate or a pharmaceutical acceptable salt thereof, the [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 3-[(2S)-2,3-bis(nitrooxy)propoxy] propanoate or a pharmaceutical acceptable salt thereof, or the 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy] propanoate or a pharmaceutical acceptable salt thereof can be administered generally within a range of 3.0 μg/eye to 600 μg/eye daily administered from one to several times a day.

For the prostaglandin analogs, in the case of latanoprost, a daily dose ranging from 0.15 μg/eye to 15 μg/eye is generally used, in the case of bimatoprost, a daily dose ranging from 0.30 μg/eye to 90 μg/eye is generally used, in the case of travoprost, a daily dose ranging from 0.12 μg/eye to 12 μg/eye is generally used, and in the case of tafluprost, a daily dose ranging from 0.045 μg/eye to 4.4 μg/eye is generally used.

The dose of the nitric oxide releasing phosphodiesterase type 5 inhibitor or of the prostaglandin analog can be appropriately raised or lowered depending on the age and symptoms of the patients and the like.

Regarding the mode of administration, the NO-PDE5 inhibitor and the prostaglandin analog can be formulated in a single preparation and administered as a mixture, or the NO-PDE5 inhibitor and the prostaglandin analog can be formulated in separate dosage forms as a kit for simultaneous or separate administration of the single compounds.

Another embodiment of the present invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 6-(nitrooxy)hexanoate or a pharmaceutically acceptable salt thereof and a prostaglandin analog selected from latanoprost, bimatoprost, travoprost or tafluprost for use in a method of treating glaucoma, ocular hypertension or a disease or a condition associated with elevated intraocular pressure.

Another embodiment of the present invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 6-(nitrooxy)hexanoate or a pharmaceutically acceptable salt thereof and a prostaglandin analog selected from latanoprost, bimatoprost, travoprost or tafluprost for use in a method of reducing intraocular pressure in condition of normal tension glaucoma.

Another embodiment of the present invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 3-[(2S)-2,3-bis(nitrooxy) propoxy]propanoate or a pharmaceutically acceptable salt thereof and a prostaglandin analog selected from latanoprost, bimatoprost, travoprost or tafluprost for use in a method of treating glaucoma, ocular hypertension or a disease or a condition associated with elevated intraocular pressure.

Another embodiment of the present invention provides ophthalmic compositions comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl] methyl 3-[(2S)-2,3-bis(nitrooxy) propoxy]propanoate or a pharmaceutically acceptable salt thereof and a prostaglandin analog selected from latanoprost, bimatoprost, travoprost or tafluprost for use in a method of reducing intraocular pressure in condition of normal tension glaucoma.

Another embodiment of the present invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate or a pharmaceutically acceptable salt thereof and a prostaglandin analog selected from latanoprost, bimatoprost, travoprost or tafluprost for use in a method of treating glaucoma, ocular hypertension or a disease or a condition associated with elevated intraocular pressure.

Another embodiment of the present invention provides ophthalmic compositions comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate or a pharmaceutically acceptable salt thereof and a prostaglandin analog selected from latanoprost, bimatoprost, travoprost or tafluprost for use in a method of reducing intraocular pressure in condition of normal tension glaucoma.

Glaucoma in the present invention includes primary open angle glaucoma, normal tension glaucoma, hypersecretion glaucoma, acute angle-closure glaucoma, chronic closed angle glaucoma, combined-mechanism glaucoma, corticosteroid glaucoma, amyloid glaucoma, neovascular glaucoma, malignant glaucoma, capsular glaucoma, plateau iris syndrome and drug induced ocular hypertension.

In the present invention a disease or a condition associated with elevated intraocular pressure includes drug-induced elevated intraocular pressure (i.e. steroid and anti-VEGF induced elevated IOP) that occurs, for example, during the treatment of retinopathies including retinopathy of prematurity, retinal vein occlusion or diabetic macular edema or age-related macular degeneration.

The present invention is also directed to methods of treating and controlling ocular hypertension associated with glaucoma, or of treating ocular hypertension or disease or a condition associated with elevated intraocular pressure. Said methods comprise topically applying to the eye(s) of the patient a therapeutically effective amount of a composition according to the present invention. Alternative said methods comprise topically applying to the eye(s) of the patient a therapeutically effective amount of Compound (1) or Compound (1A) or Compound (2) or pharmaceutically acceptable salts thereof, simultaneously, separately or sequentially to the application of the prostaglandin analog selected from latanoprost, bimatoprost, travoprost or tafluprost.

The present invention is also directed to a method to reduce intraocular pressure in a patient with normal tension glaucoma. This method comprises applying to the affected eye(s) of the patient a therapeutically effective amount of a composition according to the present invention. Alternatively, this method comprises applying to the affected eye(s) of the patient a therapeutically effective amount of Compound (1) or Compound (1A) or Compound (2) or pharmaceutically acceptable salts thereof, simultaneously, separately or sequentially to the application of the prostaglandin analog selected from latanoprost, bimatoprost, travoprost or tafluprost.

The frequency and amount of dosage will be determined by the clinician based on various clinical factors.

Another embodiment of the present invention provides ophthalmic pharmaceutical formulations comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy) hexanoate or a salt thereof, a prostaglandin analog selected from latanoprost, bimatoprost, travoprost or tafluprost and at least a pharmaceutically acceptable excipient and/or vehicle.

Another embodiment of the present invention provides ophthalmic pharmaceutical formulations comprising [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy)propoxy]propanoate or a pharmaceutically acceptable salt thereof, a prostaglandin analog selected from latanoprost, bimatoprost, travoprost or tafluprost and at least a pharmaceutically acceptable excipient and/or vehicle.

Another embodiment of the present invention provides ophthalmic pharmaceutical formulations comprising 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis (nitrooxy)propoxy]propanoate or a pharmaceutically acceptable salt thereof, a prostaglandin analog selected from latanoprost, bimatoprost, travoprost or tafluprost and at least a pharmaceutically acceptable excipient and/or vehicle.

The ophthalmic pharmaceutical formulations containing a [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate or a pharmaceutically acceptable salt thereof, or a [(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 3-[(2S)-2,3-bis(nitrooxy) propoxy]propanoate or a pharmaceutically acceptable salt thereof, or 2-{4-[3-(5-ethyl-4-oxo-7-propyl-4,5-dihydro-3H-pyrrolo[3,2-d]pyrimidin-2-yl)-4- propoxybenzene-1-sulfonyl] piperazin-1-yl}ethyl 3-[(2S)-2,3-bis(nitrooxy)propoxy]propanoate or a salt thereof, and the prostaglandin analog and at least a pharmaceutically acceptable excipients and/or vehicle can be prepared according to known methods.

In the ophthalmic pharmaceutical formulations of the invention Compound (1) or Compound (1A) or Compound (2) or pharmaceutically acceptable salts thereof and the prostaglandin analog may be combined in a single unit dosage form or in two separate unit dosage forms.

Another embodiment of the present invention provides a kit comprising: i) a nitric oxide releasing phosphodiesterase type 5 inhibitor selected from:

[(2S)-1-(4-{[(3-chloro-4-methoxyphenyl)methyl] amino}-5-{[(pyrimidin-2-yl)methyl] carbamoyl}pyrimidin-2-yl)pyrrolidin-2-yl]methyl 6-(nitrooxy)hexanoate or a pharmaceutically acceptable salt thereof,

[(2S)-1-(4-{[(3-chloro-4-methoxyphenyl)methyl] amino}-5-{[(pyrimidin-2-yl)methyl] carbamoyl}pyrimidin-2-yl)pyrrolidin-2-yl]methyl 3-[(2S)-2,3-bis(nitrooxy)propoxy]propanoate or a pharmaceutically acceptable salt thereof, or 2-{4-[3-(5-Ethyl-4-oxo-7-propyl-4,5-dihydro-3H-pyrrolo [3,2-d]pyrimidin-2-yl)-4-propoxybenzene-1-sulfonyl] piperazin-1-yl}ethyl 3-[(2S)-2,3-bis(nitrooxy) propoxy]propanoate or a pharmaceutically acceptable salt thereof, ii) a prostaglandin analog selected from: latanoprost, bimatoprost, travoprost or tafluprost, for simultaneous or separate administration of the nitric oxide releasing phosphodiesterase type 5 inhibitor and of the prostaglandin analog.

EXPERIMENTAL PART

Example 1

Synthesis of [(2S)-1-(4-{[(3-chloro-4-methoxyphenyl)methyl]amino}-5-{[(pyrimidin-2-yl)methyl] carbamoyl}pyrimidin-2-yl)pyrrolidin-2-yl]methyl 6-(nitrooxy)hexanoate (Compound 1)

To a solution of avanafil (1.00 g, 2.07 mmol) in dry dichloromethane (15 ml), 4-dimethylaminopyridine (DMAP) (252 mg, 2.07 mmol), dicyclohexylcarbodiimide (DCC) (512 mg, 2.48 mmol) and 6-(nitrooxy)hexanoic acid (440 mg, 2.48 mmol) were added.

The mixture was stirred overnight at room temperature and then diluted with dichloromethane and water. The two phases were separated and the aqueous layer was extracted twice with dichloromethane. The combined organic extracts were dried over $MgSO_4$ and concentrated under reduced pressure. The residue was purified by reversed-phase chromatography ($H_2O/CH_3CN$ with 0.1% formic acid, from 70:30 to 40:60).

The residue was taken up in dichloromethane and this solution was washed with an aqueous saturated solution of $NaHCO_3$. Then, the aqueous layer was extracted twice with dichloromethane. The combined organic phases were dried over $MgSO_4$ and concentrated under reduced pressure, giving 1.23 g of the desired product (yield: 93.0%).

$^1H$ NMR (400 MHz, DMSO-$d_6$) δ 9.19 (s, 1H), 8.81 (m, 1H), 8.75 (d, J=4.9 Hz, 2H), 8.54 (m, 1H), 7.50-7.14 (m, 3H), 7.06 (s, 1H), 4.54 (m, 4H), 4.37-3.90 (m, 3H), 3.81 (s, 3H), 3.59-3.39 (m, 4H), 2.32 (t, J=7.1 Hz, 2H), 2.09-1.73 (m, 4H), 1.66-1.52 (m, 4H), 1.32 (dt, J=5.2, 7.5 Hz, 2H).

Example 2

Synthesis of 2-hydroxypropane-1,2,3-tricarboxylic acid [(2S)-1-(4-{[(3-chloro-4-methoxyphenyl) methyl]amino}-5-{[(pyrimidin-2-yl)methyl] carbamoyl}pyrimidin-2-yl)pyrrolidin-2-yl]methyl 6-(nitrooxy)hexanoate (1/1) (Formula 1a)

(1a)

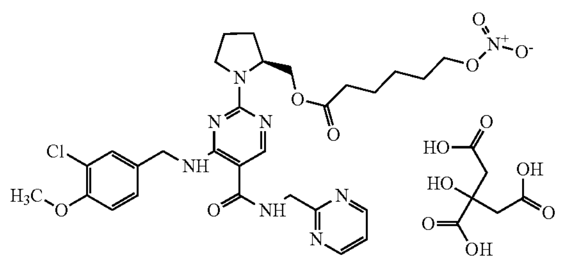

To a solution containing [(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 6-(nitrooxy)hexanoate prepared as described in Example 1, (100 mg, 0.155 mmol) and methanol (1.5 ml), citric acid monohydrate (33 mg, 0.155 mmol) was added. The mixture was stirred for 10 minutes at room temperature, then concentrated and the solid washed with methyl tert-butyl ether (MTBE). The solid was filtered and dried under reduced pressure, giving 125 mg of the desired product (crude yield: 96.6%).

$^1H$ NMR (600 MHz, DMSO-d6) δ 12.39-12.36 (m, 3H), 9.19 (s, 1H), 8.80 (m, 1H), 8.75 (d, J=4.9 Hz, 2H), 8.53 (m, 1H), 7.42-7.15 (m, 3H), 7.06 (m, 1H), 4.65-4.38 (m, 6H), 4.37-4.11 (m, 3H), 3.80 (s, 3H) 3.59-3.39 (m, 2H), 2.75 (d, J=15.4 Hz, 2H), 2.65 (d, J=15.4 Hz, 2H), 2.32 (m, 2H), 2.05-1.80 (m, 4H), 1.47-1.08 (m, 4H), 1.32 (q, 2H)

Example 3

Synthesis of (2E)-but-2-enedioic acid [(2S)-1-(4-{[(3-chloro-4-methoxyphenyl) methyl]amino}-5-{[(pyrimidin-2-yl)methyl]carbamoyl}pyrimidin-2-yl) pyrrolidin-2-yl]methyl 6-(nitrooxy)hexanoate (1/1) (Formula 1b)

(1b)

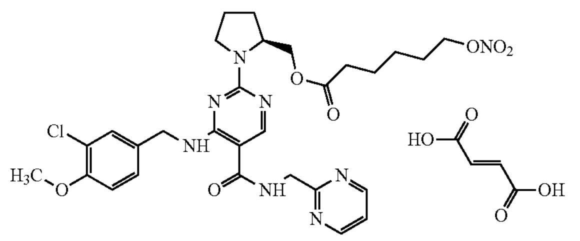

To a solution containing [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate prepared as described in Example 1, (100 mg, 0.155 mmol) and methanol (1.5 ml), fumaric acid (18 mg, 0.155 mmol) was added. The mixture was stirred 10 minutes at room temperature, then concentrated and the solid washed with methyl tert-butyl ether. The solid was filtered and dried under reduced pressure, yielding 103 mg of (2E)-but-2-enedioic acid [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy) hexanoate (1/1) (yield: 87%).

$^1$H NMR (600 MHz, DMSO-d6) δ 13.13 (m, 2H), 9.17 (m, 1H), 8.76 (m, 3H), 8.54 (m, 1H), 7.38 (m, 1H), 7.24 (m, 2H), 7.04 (m, 1H), 6.63 (s, 2H), 4.52 (m, 5H), 4.20 (m, 2H), 3.81 (s, 3H), 3.52 (m, 2H), 3.32 (m, 2H), 2.31 (m, 2H), 1.92 (m, 4H), 1.64 (m, 2H), 1.50 (m, 2H), 1.32 (m, 2H).

Example 4

Synthesis of (2Z)-but-2-enedioic acid-[(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate (1/1) (Formula 1c)

(1c)

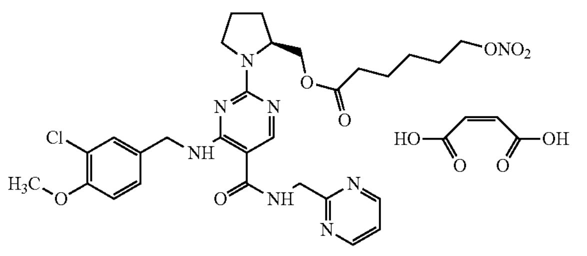

To a solution containing [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy)hexanoate prepared as described in Example 1, (100 mg, 0.155 mmol) and methanol (1.5 ml), maleic acid (18 mg, 0.155 mmol) was added. The mixture was stirred 10 minutes at room temperature, then concentrated and the solid washed with methyl tert-butyl ether. The solid was filtered and dried under reduced pressure, giving 113 mg of (2Z)-but-2-enedioic acid [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 6-(nitrooxy) hexanoate (1/1) (yield: 96%).

$^1$H NMR (600 MHz, DMSO-d6) δ 12.35 (m, 2H), 9.18 (m, 1H), 8.77 (m, 3H), 8.54 (s, 1H), 7.38 (m, 2H), 7.22 (m, 1H), 7.04 (m, 1H), 6.33 (s, 2H), 4.55 (m, 6H), 4.20 (m, 2H), 3.98 (m, 1H), 3.80 (s, 3H), 3.49 (m, 2H), 2.31 (m, 2H), 1.92 (m, 4H), 1.56 (m, 4H), 1.32 (m, 2H).

Example 5

Synthesis of [(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis (nitrooxy)propoxy]propanoate (Compound (1A))

Synthesis of 4-nitrophenyl 3-[(2S)-2,3-bis(nitrooxy)propoxy]propanoate

Step 1: Synthesis of (S)-4-(allyloxymethyl)-2,2-dimethyl-1,3-dioxolane

NaH (60%) (3.4 g; 85.54 mmol) was suspended in dry THF (140 ml) together with S(+)-1,2-isopropylidenglycerol (5.65 g; 42.75 mmol) and 15-Crown-5 (0.9 g; 4.28 mmol). The mixture was cooled to 0° C. and allyl bromide (7.2 ml; 85.54 mmol) was added dropwise. The suspension was stirred for 6 h at rt, then $NH_4Cl$ saturated solution (100 ml) was added dropwise at 0° C. and then the mixture extracted with $Et_2O$ (3×100 ml). The combined organic layers were washed once with brine and concentrated under reduced pressure carefully. The residue was purified by flash chromatography (Biotage SP4 instrument, SNAP 100 column, isocratic elution $Et_2O$/Cyclohexane 1:9), affording 5.8 g, (yield 78.5%) of the title compound ((S)-4-(allyloxymethyl)-2,2-dimethyl-1,3-dioxolane).

$^1$H NMR (300 MHz, Chloroform-d) δ 6.00-5.78 (m, 1H), 5.35-5.13 (m, 2H), 4.35-4.21 (m, 1H), 4.11-3.98 (m, 3H), 3.73 (m, 1H), 3.57-3.40 (m, 2H), 1.51-1.32 (m, 6H).

Step 2: Synthesis of (S)-3-((2,2-dimethyl-1,3-dioxolan-4-yl)methoxy)propan-1-ol To a stirred solution of (S)-4-(allyloxymethyl)-2,2-dimethyl-1,3-dioxolane (2.0 g, 10.64 mmol) in dry THF (180 ml) cooled at 0° C., 9-borabicyclo[3.3.1]nonane (9BBN) 0.5M (241.8 ml, 121 mmol) was added dropwise. The reaction was stirred 30 minutes at 0° C. and overnight at room temperature. The reaction mixture was cooled at 0° C. and NaOH 2N (84 ml) was added together with $H_2O_2$ 30% (58 ml). The mixture was diluted with $Et_2O$ (100 ml) and NaOH 1N (100 ml). The 2 phases were separated and aqueous layer was extracted with $Et_2O$ (3×120 ml). The combined organic layers were washed once with brine, dried over $Na_2SO_4$ and concentrated under reduced pressure. The residue was purified by flash chromatography (Biotage SP4 instrument, SNAP 100 column, ethyl Acetate in cyclohexane, from 30% to 80% in 10 c.v. affording 6.4 g (yield: 100%) of the title compound ((S)-3-((2,2-dimethyl-1,3-dioxolan-4-yl)methoxy)propan-1-ol).

$^1$H NMR (300 MHz, Chloroform-d) δ 4.35-4.20 (m, 1H), 4.11-4.01 (m, 1H), 3.85-3.63 (m, 5H), 3.58-3.46 (m, 2H), 1.97-1.80 (m, 2H), 1.45 (s, 3H), 1.38 (s, 3H).

Step 3: Synthesis of (S)-3-((2,2-dimethyl-1,3-dioxolan-4-yl)methoxy)propanoic acid To a solution of (S)-3-((2,2-dimethyl-1,3-dioxolan-4-yl)methoxy)propan-1-ol (2.03 g; 10.51 mmol) in acetone (50 ml) cooled at 0° C., $NaHCO_3$ sat solution (56 ml), NaBr (0.45 g, 4.37 mmol) and 2,2,6,6-Tetramethylpiperidin-1-oxyl (TEMPO) (0.34 g, 2.17 mmol) were added. Trichloroisocyanuric acid (4.91 g, 21.12 mmol) was then added portionwise. The mixture was allowed to reach room temperature and stirred for 3 h. The mixture was then cooled at 0° C. and isopropanol (20 ml) was added slowly. The mixture was stirred at 0° C. 30 minutes. The formation of a white solid was observed. The precipitate was filtered off and the solvent concentrated. NaOH 2N was added to the residue (pH=12) and the aqueous solution was washed twice with ethyl acetate. To the aqueous phase HCl 1N was added until pH 2-3 and it was extracted with ethyl acetate (5×50 ml). The combined organic phases were dried over $Na_2SO_4$ and then evaporated affording 0.82 g (Yield: 38%) of the title compound ((S)-3-((2,2-dimethyl-1,3-dioxolan-4-yl) methoxy)propanoic acid).

$^1$HNMR (300 MHz, Chloroform-d) δ 4.34-4.16 (m, 1H), 4.11-3.97 (m, 1H), 3.85-3.68 (m, 3H), 3.63-3.42 (m, 2H), 2.74-2.55 (m, 2H), 1.41 (s, 3H), 1.35 (s, 3H).

Step 4: Synthesis of (S)-4-nitrophenyl 3-((2,2-dimethyl-1,3-dioxolan-4-yl)methoxy) propanoate To a solution of (S)-3-((2,2-dimethyl-1,3-dioxolan-4-yl) methoxy)propanoic acid (0.82 g, 4.02 mmol), dicyclohexylcarbodiimide (DCC) (0.83 mg, 4.02 mmol) and 4-dimethylaminopyridine (DMAP) (0.1 g, 0.80 mmol) in dichloromethane (15 ml), 4-nitrophenol (0.56 g; 4.02 mmol) was added portionwise. The mixture was stirred overnight at room temperature, then the precipitate was filtered off and the solvent evaporated. The residue was purified by flash chromatography (Biotage SP4 instrument, ethyl acetate in cyclohexane from 5% to 50% in 12 CV) affording 0.97 g of the title compound ((S)-4-nitrophenyl 3-((2,2-dimethyl-1,3-dioxolan-4-yl)methoxy) propanoate) (Yield: 74%).

$^1$H NMR (300 MHz, Chloroform-d) δ 8.33-8.21 (m, 2H), 7.37-7.20 (m, 2H), 4.37-4.20 (m, 1H), 4.09-4.00 (m, 1H), 3.96-3.84 (m, 2H), 3.80-3.66 (m, 1H), 3.63-3.47 (m, 2H), 2.96-2.78 (m, 2H), 1.42 (s, 3H), 1.36 (s, 3H).

Step 5: Synthesis of (R)-4-nitrophenyl 3-(2,3-dihydroxypropoxy) propanoate

To a stirred solution of (S)-4-nitrophenyl 3-((2,2-dimethyl-1,3-dioxolan-4-yl)methoxy)propanoate (0.97 g, 2.97 mmol) in THE (10 ml), HCl 3N (2 ml) was added and the solution stirred for 4 h at room temperature. Then ethyl acetate (5 ml) and $H_2O$ (5 ml) were added and the two phases were separated. The aqueous phase was extracted with ethyl acetate (2×5 ml). The combined organic layers were washed with brine, dried over $Na_2SO_4$ and concentrated under reduced pressure affording 0.89 g of the title compound ((R)-4-nitrophenyl 3-(2,3-dihydroxypropoxy) propanoate, which was used in the next step without further purification.

Step 6: Synthesis of 4-nitrophenyl 3-[(2S)-2,3-bis (nitrooxy)propoxy]propanoate

To a solution of acetic anhydride (0.76 ml, 8.07 mmol) in dichloromethane (5 ml) at −40° C., fuming $HNO_3$ (0.38 ml, 9.32 mmol) was added dropwise. A solution of (R)-4-nitrophenyl 3-(2,3-dihydroxypropoxy)propanoate (0.89 g, 3.11 mmol) in dichloromethane (7 ml) was then added dropwise. The mixture was allowed to reach 0° C. and stirred for 4 hours. The mixture was then poured into ice and $NaHCO_3$ was added portion wise. The two phases were separated and the aqueous phase washed twice with dichloromethane. The combined organic phases were dried over $Na_2SO_4$ and concentrated affording 0.56 g of 4-nitrophenyl 3-[(2S)-2,3-bis(nitrooxy)propoxy]propanoate (yield of two steps: 38%).

$^1$H NMR (300 MHz, Chloroform-d) δ 8.35-8.22 (m, 2H), 7.35-7.22 (m, 2H), 5.48-5.34 (m, 1H), 4.88-4.73 (m, 1H), 4.73-4.56 (m, 1H), 3.94-3.85 (m, 2H), 3.85-3.77 (m, 2H), 2.88 (t, 2H).

Synthesis of [(2S)-1-(4-{[(3-chloro-4-methoxyphenyl)methyl]amino}-5-{[(pyrimidin-2-yl)methyl] carbamoyl}pyrimidin-2-yl)pyrrolidin-2-yl]methyl 3-[(2S)-2,3-bis (nitrooxy)propoxy]propanoate To a solution of Avanafil (160 mg, 0.331 mmol) and 4-nitrophenyl 3-[(2S)-2,3-bis(nitrooxy)propoxy]propanoate (82 mg, 0.218 mmol) in dry dichloromethane (1.5 ml), 4-dimethylaminopyridine (DMAP) (40 mg, 0.327 mmol) was added.

The mixture was stirred over weekend at room temperature, then diluted with dichloromethane and water. The two phases were separated and the aqueous phase extracted twice with dichloromethane. The combined organic phases were dried over $MgSO_4$ and concentrated under reduced pressure. The residue was purified by reversed-phase chromatography ($H_2O/CH_3CN$ with 0.1% formic acid, from 85:15 to 55:45).

After purification dichloromethane and a saturated solution of $NaHCO_3$ were added to the residue. The two phases were separated and the aqueous phase extracted twice with dichloromethane. The combined organic phases were dried over $MgSO_4$ and concentrated under reduced pressure, giving 227 mg of the product (yield: 95.0%).

$^1$H NMR (400 MHz, DMSO-$d_6$) δ 9.16 (t, J=6.0 Hz, 1H), 8.78 (m, 3H), 8.75 (d, J=4.9 Hz, 1H), 8.53 (s, 1H), 7.38 (t, J=4.9 Hz, 1H), 7.34-7.16 (m, 1H), 7.05 (t, J=9.4 Hz, 1H), 5.55 (m, 1H), 4.89 (d, J=12.9 Hz, 1H), 4.75 (m, 1H), 4.54 (m, 4H), 4.41-3.93 (m, 3H), 3.80 (s, 3H), 3.78-3.63 (m, 4H), 3.51 (m, 2H), 2.57 (t, J=6.1 Hz, 2H), 1.92 (m, 4H).

Example 6

Preparation of 2-hydroxypropane-1,2,3-tricarboxylic acid [(2S)-1-(4-{[(3-chloro-4-methoxyphenyl) methyl]amino}-5-{[(pyrimidin-2-yl)methyl] carbamoyl}pyrimidin-2-yl)pyrrolidin-2-yl]methyl 3-[(2S)-2,3-bis(nitrooxy)propoxy]propanoate (1/1) (Formula (1A.a))

(1A.a)

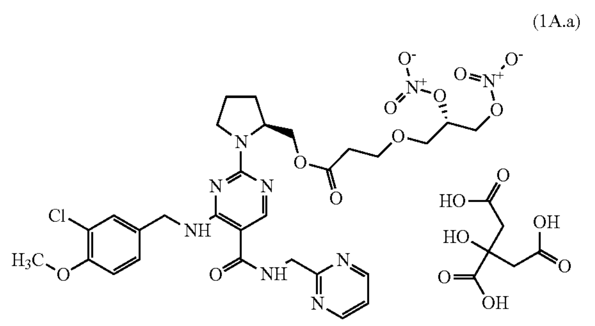 [SMILES: COc1ccc(CNc2nc(N3CCC[C@H]3COC(=O)CCOC[C@@H](CO[N+](=O)[O-])O[N+](=O)[O-])ncc2C(=O)NCc2ncccn2)cc1Cl ; O=C(O)CC(O)(CC(=O)O)C(=O)O]

To a solution of [(2S)-1-(4-{[(3-chloro-4-methoxyphenyl) methyl]amino}-5-{[(pyrimidin-2-yl)methyl] carbamoyl}pyrimidin-2-yl)pyrrolidin-2-yl]methyl 3-[(2S)-2,3-bis(nitrooxy)propoxy]propanoate prepared as described in Example 5 (227 mg, 0.315 mmol) in methanol (2 ml), citric acid monohydrate (66 mg, 0.315 mmol) was added. The mixture was stirred for 10 minutes at room temperature, then concentrated and the residue was washed with diethyl ether. The solid was filtered and dried under reduced pressure, giving 280 mg of the title product (crude yield: 97.4%).

$^1H$ NMR (600 MHz, DMSO-d6) δ 12.35 (s, 3H), 9.18 (s, 1H), 8.77 (m, 3H), 8.55 (m, 1H), 7.46-7.33 (m, 2H), 7.34-7.17 (m, 1H), 7.06 (dd, J=16.6, 8.3 Hz, 1H), 5.55 (s, 1H), 4.81 (m, 4H), 4.63-4.42 (m, 4H), 4.38-3.96 (m, 3H), 3.81 (s, 3H), 3.71 (m, 2H), 3.57-3.42 (m, 2H), 2.75 (d, J=15.4 Hz, 2H), 2.65 (d, J=15.4 Hz, 2H), 2.57 (t, J=5.9 Hz, 2H), 1.92 (m, 4H).

Example 7

Synthesis of 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate (Compound (2))

To a solution of Mirodenafil (500 mg, 0.940 mmol) and 4-nitrophenyl 3-[(2S)-2,3-bis(nitrooxy)propoxy]propanoate prepared as described in Example 5, (423 mg, 1.128 mmol) in dry dichloromethane (5 ml), 4-dimethylaminopyridine (DMAP) (115 mg, 0.940 mmol) was added.

The mixture was stirred at room temperature for 48 h, then it was diluted with dichloromethane and water. The two phases were separated and the aqueous phase extracted twice with dichloromethane. The combined organic phases were dried over $MgSO_4$ and concentrated under reduced pressure. The residue was purified by reversed-phase chromatography ($H_2O/CH_3CN$ with 0.1% formic acid, from 70:30 to 20:80).

After purification dichloromethane and a saturated solution of $NaHCO_3$ were added to the residue. The two phases were separated and the aqueous phase extracted twice with dichloromethane. The combined organic phases were dried over $MgSO_4$ and concentrated under reduced pressure, giving 540 mg of 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy) propoxy]propanoate (yield: 75.0%).

$^1H$ NMR (400 MHz, DMSO-d6) δ 11.67 (s, 1H), 7.88 (d, J=2.4 Hz, 1H), 7.80 (dd, J=8.8, 2.4 Hz, 1H), 7.38 (d, J=8.9 Hz, 1H), 7.31 (s, 1H), 5.50-5.56 (m, 1H), 4.88 (dd, J=12.8, 3.0 Hz, 1H), 4.72 (dd, J=12.8, 6.5 Hz, 1H), 4.37 (q, J=7.1 Hz, 2H), 4.00-4.15 (m, 4H), 3.60-3.75 (m, 4H), 2.89 (br s, 4H), 2.51-2.60 (m, 10H), 1.58-1.79 (m, 4H), 1.36 (t, J=7.1 Hz, 3H), 0.96 (br t, J=7.4 Hz, 3H), 0.92 ppm (t, J=7.3 Hz, 3H).

Example 8

Synthesis of 2-hydroxypropane-1,2,3-tricarboxylic acid 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis (nitrooxy)propoxy]propanoate (1/1) (Formula (2a))

(2a)

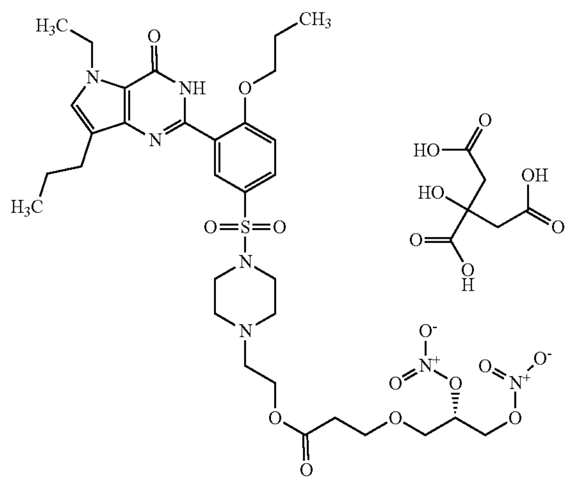

2-{4-[3-(5-ethyl-4-oxo-7-propyl-4,5-dihydro-3H-pyrrolo [3,2-d]pyrimidin-2-yl)-4-propoxybenzene-1-sulfonyl]piperazin-1-yl}ethyl 3-[(2S)-2,3-bis(nitrooxy)propoxy]propanoate (295 mg, 0.384 mmol) was re-dissolved in methanol (1.5 ml), and citric acid monohydrate (81 mg, 0.384 mmol) was added. The mixture was stirred for 10 minutes at room temperature, then concentrated and the solid washed with diethyl ether. The solid was filtered and dried under reduced pressure, giving 361 mg of the title compound (crude yield: 98%).

$^1H$ NMR (400 MHz, DMSO-d6) δ 12.30 (bs, 3H), 11.67 (s, 1H), 7.89 (d, J=2.4 Hz, 1H), 7.80 (dd, J=8.8, 2.5 Hz, 1H), 7.38 (d, J=8.9 Hz, 1H), 7.31 (s, 1H), 5.53 (m, J=10.3, 6.7, 3.9 Hz, 1H), 4.88 (dd, J=12.8, 3.0 Hz, 1H), 4.72 (dd, J=12.9, 6.5 Hz, 1H), 4.37 (q, J=7.1 Hz, 2H), 4.10 (dt, J=11.4, 6.0 Hz, 4H), 3.77-3.58 (m, 4H), 2.90 (s, 4H), 2.75 (d, J=15.4 Hz, 2H), 2.65 (d, J=15.4 Hz, 2H), 2.61-2.52 (m, 10H), 1.80-1.58 (m, 4H), 1.36 (t, J=7.1 Hz, 3H), 0.97 (t, 3H), 0.94 (t, 3H).

Example 9

Synthesis of 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis (nitrooxy)propoxy]propanoate hydrogen chloride (1/2) (Formula (2b))

(2b)

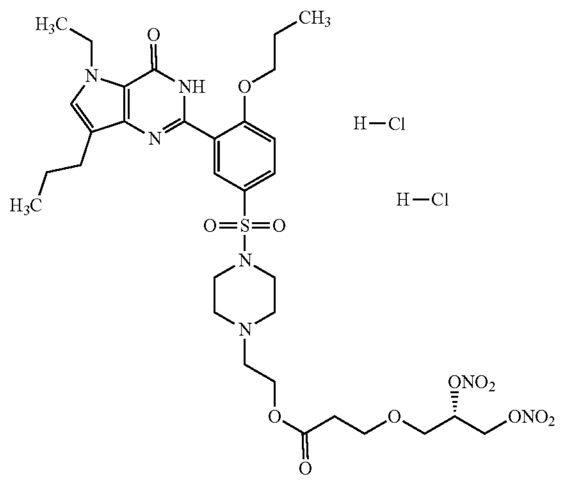

To a solution containing 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl 3-[(2S)-2,3-bis(nitrooxy)propoxy]propanoate prepared as disclosed in Example 7 (72 mg, 0.094 mmol) in methanol (1.0 ml), HCl 3M methanolic solution (63 uL, 0.188 mmol) was added. The mixture was stirred for 10 minutes at room temperature, then concentrated and the solid washed with $Et_2O$. The solid was filtered and dried under reduced pressure, giving 68 mg of the title compound (yield: 86%).

$^1$H NMR (600 MHz, DMSO-d6) δ 11.73 (s, 1H), 11.05 (s, 1H), 8.07-7.76 (m, 2H), 7.42 (d, J=8.7 Hz, 1H), 7.32 (s, 1H), 5.59-5.52 (m, 1H), 4.90 (dd, J=12.8, 2.8 Hz, 1H), 4.75 (dd, J=12.8, 6.5 Hz, 1H), 4.38 (q, J=7.1 Hz, 3H), 4.14 (t, J=6.3 Hz, 2H), 3.77-3.66 (m, 6H), 2.60-2.49 (m, 14H), 1.80-1.72 (m, 2H), 1.69-1.60 (m, 2H), 1.36 (t, J=7.2 Hz, 3H), 0.97 (t, J=7.4 Hz, 3H), 0.93 (t, J=7.3 Hz, 3H).

The invention claimed is:

1. An ophthalmic composition comprising:

i) a nitric oxide releasing phosphodiesterase type 5 inhibitor selected from:

[(2S)-1-(4-{[(3-chloro-4-methoxyphenyl)methyl] amino}-5-{[(pyrimidin-2-yl)methyl] carbamoyl}pyrimidin-2-yl) pyrrolidin-2-yl]methyl 6-(nitrooxy) hexanoate or a pharmaceutically acceptable salt thereof, and ii) a prostaglandin analog selected from: latanoprost, bimatoprost, travoprost or tafluprost.

2. The composition according to claim 1 wherein the nitric oxide releasing phosphodiesterase type 5 inhibitor is a pharmaceutically acceptable salt selected from:

2-hydroxypropane-1,2,3-tricarboxylic acid [(2S)-1-(4-{[(3-chloro-4-methoxyphenyl)methyl]amino}-5-{[(pyrimidin-2-yl)methyl]carbamoyl}pyrimidin-2-yl) pyrrolidin-2-yl]methyl 6-(nitrooxy) hexanoate (1/1), or (2E)-but-2-enedioic acid [(2S)-1-(4-{[(3-chloro-4-methoxyphenyl)methyl]amino}-5-{[(pyrimidin-2-yl) methyl]carbamoyl}pyrimidin-2-yl) pyrrolidin-2-yl] methyl 6-(nitrooxy) hexanoate (1/1), or (2Z)-but-2-enedioic acid [(2S)-1-(4-{[(3-chloro-4-methoxyphenyl)methyl]amino}-5-{[(pyrimidin-2-yl) methyl]carbamoyl}pyrimidin-2-yl) pyrrolidin-2-yl] methyl 6-(nitrooxy) hexanoate (1/1).

3. The composition according to claim 1, wherein the prostaglandin analog is latanoprost.

4. The composition according to claim 1, wherein the prostaglandin analog is bimatoprost.

5. The composition according to claim 1, wherein the prostaglandin analog is travoprost.

6. The composition according to claim 1, wherein the prostaglandin analog is tafluprost.

7. A method of treating glaucoma, ocular hypertension or a disease or a condition associated with elevated intraocular pressure comprising administering the ophthalmic composition according to claim 1 to a subject in need thereof.

8. The method according to claim 7 wherein the condition associated with elevated intraocular pressure is drug-induced elevated intraocular pressure that occurs during the treatment of retinopathies, wherein the retinopathies are selected from the group consisting of retinopathy of prematurity, retinal vein occlusion, diabetic macular edema or age-related macular degeneration, and combinations thereof.

9. A method of treating normal tension glaucoma comprising administering the ophthalmic composition according to claim 1 to a subject in need thereof.

10. The method according to claim 7, wherein the nitric oxide releasing phosphodiesterase type 5 inhibitor or a pharmaceutically acceptable salt thereof is applied to eye(s), simultaneously, separately or sequentially to the application of the prostaglandin analog to the eye(s).

11. An ophthalmic pharmaceutical formulation comprising the composition according to claim 1, and at least a pharmaceutically acceptable excipient and/or vehicle.

12. A kit comprising:

i) a nitric oxide releasing phosphodiesterase type 5 inhibitor selected from:

[(2S)-1-(4-{[(3-chloro-4-methoxyphenyl)methyl] amino}-5-{[(pyrimidin-2-carbamoyl}pyrimidin-2-yl)pyrrolidin-2-yl]methyl 6-(nitrooxy)hexanoate yl)methyl] or a pharmaceutically acceptable salt thereof, and ii) a prostaglandin analog selected from: latanoprost, bimatoprost, travoprost or tafluprost, for simultaneous or separate administration of the nitric oxide releasing phosphodiesterase type 5 inhibitor and of the prostaglandin analog.

* * * * *